United States Patent [19]

Drent

[11] Patent Number: 4,739,107

[45] Date of Patent: Apr. 19, 1988

[54] PROCESS FOR THE PREPARATION OF A DIESTER OF A DICARBOXYLIC ACID

[75] Inventor: Eit Drent, Amsterdam, Netherlands

[73] Assignee: Shell Oil Company, Houston, Tex.

[21] Appl. No.: 2,488

[22] Filed: Jan. 12, 1987

[30] Foreign Application Priority Data

Jan. 29, 1986 [GB] United Kingdom ............... 8602177

[51] Int. Cl.$^4$ ............................................ C07C 67/38
[52] U.S. Cl. ........................... 560/204; 502/102;
502/150; 502/326; 502/330; 502/170; 502/331;
560/81; 560/97; 560/114; 560/121; 560/123;
560/124; 560/127; 562/497; 562/522
[58] Field of Search ................. 560/81, 97, 204, 114,
560/121, 123, 124, 127; 502/102, 150, 170, 326,
330, 331; 562/497, 522

[56] References Cited

U.S. PATENT DOCUMENTS

| | | | |
|---|---|---|---|
| 3,076,032 | 1/1963 | Riemenschneider et al. | 560/232 X |
| 3,530,168 | 9/1970 | Biale | 560/204 X |
| 3,759,984 | 9/1983 | Fujii et al. | 560/204 |
| 4,281,174 | 7/1981 | Current | 560/204 |
| 4,379,939 | 4/1983 | Radel et al. | 560/193 |

*Primary Examiner*—Werren B. Lone
*Assistant Examiner*—Vera C. Clarke

[57] ABSTRACT

Process for the preparation of dicarboxylate esters by reacting an optionally substituted ethylenically unsaturated hydrocarbon having two carbon atoms less than said dicarboxylic acid, CO and an alcohol in the presence of a Group VIII noble metal or a compound thereof, a quinone and optionally, a redox agent and molecular oxygen.

30 Claims, No Drawings

PROCESS FOR THE PREPARATION OF A DIESTER OF A DICARBOXYLIC ACID

FIELD OF THE INVENTION

The invention relates to a process for the preparation of a diester of a dicarboxylic acid.

BACKGROUND OF THE INVENTION

It is known from U.S. Pat. No. 3,759,984 to prepare succinic acid and/or derivatives thereof by reacting ethylene with carbon monoxide and an alcohol in the presence of a palladium compound having a strong scid residual group, an amino acid, and a heavy metal salt while supplying oxygen to increase the reaction rate and to prolong the catalyst life. The examples of this known process show that dimethyl succinate was obtained in a low yield, calculated on starting ethylene.

It is an object of the present invention to prepare diesters fo dicarboxylic acids in a very high yield.

SUMMARY OF THE INVENTION

This invention relates to a process for the preparation of a diester of a dicarboxylic acid which process comprises reacting an optionally substituted ethylenically unsaturated hydrocarbon having two carbon atoms per molecule less than said dicarboxylic acid, carbon monoxide and an alcohol in the presence of:
(a) a noble metal selected from Group VIII of the Periodic Table of the Elements and/or a compound thereof, and
(b) a quinone.

DESCRIPTION OF THE PREFERRED EMBODIMENTS

The noble metals which are used in the process according to the present invention are platinum, rhodium, ruthenium, palladium, iridium and/or osmium. These metals may be used in metallic form or as compounds. Mixtures of compounds of the same or different such noble metals or mixtures of such noble metals in metallic form may be used. The noble metals may be used as finely divided metals, not supported on a carrier, or supported on a carrier such as, for example, activated carbon, pumice or graphite. The present process is preferably carried out in the presence of palladium and/or a compound of palladium. Very good results have been obtained with compounds of palladium. Examples of suitable compounds of Group VIII noble metals are salts, such as nitrates, sulfates, halides, (fluorides, chlorides, bromides and iodides) and carboxylates. Among the carboxylates, salts of alkanoic acids having not more than 12 carbon atoms per molecule are preferred, particularly the Pd (II) salts. Palladium (II) acetate is most preferred.

Other examples of suitable palladium compounds are palladium complexes such as bis(2,4-pentanedionato)palladium, bis(picolinato)palladium, tetrakis(triphenylphosphine)palladium, tris(dibenzylidene-acetone)dipalladium, bis(triphenylphosphine)(1,4-benzoquinone)palladium, tetrakisacetonitrilepalladium tetrafluoroborate, bis(tri-o-tolyphosphine)palladium acetate, bis(triphenylphosphine)palladium sulfate, palladium olefin complexes, for instance di-$\mu$-chloro-dichlorobis(ethylene)dipalladium([Pd.C$_2$H$_4$.Cl$_2$]$_2$), and di-$\mu$-chlorodichlorobis(propylene)dipalladium([Pd.C$_3$H$_6$.Cl$_2$]$_2$), and palladiumhydride complexes. Palladium may be used in complex combination with phosphites, such as triphenyl phosphite or tributyl phosphite.

The quinone applied in the process according to the present invention may be an ortho-quinone or a para-quinone and may be, for example, a benzoquinone, a naphthoquinone, an anthraquinone or a chrysenequinone. Preference is given to optionally substituted benzoquinones, particularly to p-benzoquinones. According to a preferred embodiment of the present invention, halogen-substituted p-benzoquinones are present, very high yields of diesters of dicarboxylic acids being obtained. In this embodiment one or more fluorine, chlorine, bromine and/or iodine atoms are attached to the aromatic nucleus of the p-benzoquinone. Examples of such quinones are 2-iodo-, 2-bromo-, 2-chloro- and 2-fluoro-p-benzoquinone, 2,6-diiodo-, 2,6-dibromo-, 2,6-dichloro- and 2,6-difluoro-p-benzoquinone, 2,3,6-triiodo-, 2,3,6-tribromo-, 2,3,6-trichloro- and 2,3,6-trifluoro-p-benzoquinone. Tetrahalo-p-benzoquinones are preferred, particularly tetrachloro-p-benzoquinone (also referred to as "chloranil"). According to another preferred embodiment, unsubstituted p-benzoquinone is applied in the present process. Further examples of suitable quinones are 9,10-anthraquinone, 1,4-naphthoquinone, 5,6-chrysenequinone and alkyl-substituted p-benzoquinones such as 2-methyl-p-benzoquinone and 2,6-dimethyl-p-benzoquinone. Mixtures of quinones may be present such as, for example, of p-benzoquinone and a halogen-substituted p-benzoquinone.

It has, moreover, been found that the yield of diesters of dicarboxylic acids is further enhanced by carrying out the present process in the presence of a redox agent. Redox agents are well known in the art. It is generally a compound of copper, iron, vanadium, cobalt or manganese. Mixtures of such compounds may be used. These five metals are preferably used in the form of salts, such as chlorides, nitrates, sulfates, carboxylates, preferably those carboxylates having not more than 12 atoms per molecule, perchlorates and sulfonates, for example, benzenesulfonates and p-tosylates. Among the metal compounds, cupric compounds are preferred, particularly cupric tosylate and cupric perchlorate. Other examples of suitable redox agents are cobalt (II) complexes of organic ligands, cupric acetate, cupric butyrate, cupric chloride, cupric bromide, ferrous propionate, ferric acetate, ferric chloride, ferric bromide and cobalt (II) acetate. Very high yields of diesters of dicarboxylic acids have been obtained with ferrous perchlorate.

The process according to the present invention may be carried out using a molar ratio noble metal of Group VIII and/or a compound thereof to optionally substituted ethylenically unsaturated hydrocarbon which is not critical and may vary within wide ranges. This molar ratio is suitably in the range of from $10^{-2}$ to $10^{-6}$.

The process according to the present invention may be carried out using a molar ratio redox agent to noble metal of Group VIII and/or a compound thereof which is not critical and may vary within wide ranges. This molar ratio is suitably in the range of from 0.5 to 1000 and preferably from 1 to 200.

The process according to the present invention results in the formation of a diester of a dicarboxylic acid and of a hydroquinone. The hydroquinone may be isolated from the reaction mixture and, if desired, purified. The isolated and optionally purified hydroquinone may be used for any suitable purpose but is preferably oxidized in a suitable manner to the corresponding quinone, which quinone is preferably used in the process according to the present invention.

It has, furthermore, been found that the yield of diesters of dicarboxylic acids is further enhanced by carrying out the present process in the presence of molecular oxygen. The molecular oxygen may be supplied, for example, as pure oxygen, in air enriched with oxygen, in air or diluted with an inert gas such as argon. The oxygen is supplied using a molar ratio molecular oxygen to carbon monoxide which is not critical and may vary within wide ranges, preferably in the range of from 1:3 to 1:6, the stoichiometric ratio being 1:4. The oxygen may be supplied in one portion but may, for safety reasons, be supplied in portions.

The process according to the present invention can be carried out using a molar ratio quinone to optionally substituted ethylenically unsaturated hydrocarbon which is not critical and which may vary within wide limits. This molar ratio may vary, for example, in the range of from 0.001 to 5.

The process according to the present invention can be carried out using a molar ratio carbon monoxide to optionally substituted ethylenically unsaturated hydrocarbon which is not critical and may vary within wide limits, preferably in the range of from 0.5:1 to 10:1 and particularly from 1:1 to 3:1, the stoichiometric ratio being 2.

The process according to the present invention can be carried out in wide ranges of temperature and pressure, preferably in the range of from 20° C. to 200° C., more preferably from 50° C. to 125° C., and at a pressure preferably in the range of from 5 to 200 bar, more preferably from 10 to 100 bar.

The alcohol can be applied in a molar ratio alcohol to optionally substituted ethylenically unsaturated hydrocarbon which is not critical and may vary within wide limits. This molar ratio is suitably at least the stoichiometric molar ratio which is 2 and may be, if desired, in the range of from 2 to 1000.

The process according to the present invention can be carried out in the absence of or, which is preferred, in the presence of a solvent which does not inhibit the reaction. The alcohol which is used as a reactant may be used as a solvent. Very good results have been obtained with ethers. Examples of ethers are methyl ethyl ether, diethyl ether, dipropyl ether, tetrahydrofuran, dimethyl ether of diethylene glycol (also referred to as "diglyme"), methyl tertbutyl ether, dichloroethyl ether, ethyl phenyl ether, diethylene glycol diethyl ether and 1,4-dioxane. Other examples of suitable solvents are halogenated hydrocarbons such as chloroform, chlorobenzene, carbon tetrachloride and perfluoroalkanes; esters such as the methyl and ethyl esters of formic acid, acetic acid, adipic acid, succinic acid, propionic acid, oxalic acid and benzoic acid; sulfones such as dimethyl sulphone, methyl butyl sulfone and tetrahydrothiophone 1,1-dioxide (also referred to as "sulfolane"); aromatic hydrocarbons such as benzene, toluene and the three xylenes; cycloalkanes such as cyclohexane; nitrobenzene.

The process according to the present invention is suitably carried out with an optionally substituted ethylenically unsaturated hydrocarbon carrying a hydrogen atom to at least one of the double-bonded carbon atoms. Preference is given to optionally substituted alkenes having in the range of from 2 to 20 and particularly 2 to 10 carbon atoms per molecule or an optionally substituted cycloalkene having in the range of from 3 to 20 carbon atoms per molecule. Very good results have been obtained with ethylene. Other examples of suitable ethylenically unsaturated hydrocarbons are propene, 1-butene, 2-butene, isobutene, 1-pentene, 2-pentene, the n-hexenes, the n-heptenes, the n-octenes, the n-nonenes, the n-decenes, the n-decenes, the n-dodecenes, the n-eicosenes, 2-methyl-1-butene, 2-methyl-2-butene, 2-ethyl-1-butene, 2-methyl-1-pentene, 2-ethyl-3-hexane, 2-ethyl-1-octene, styrene, α-methylstyrene and allylbenzene. Further examples are cycloalkenes such as cyclopentene, cyclohexene, cycloheptene, cyclooctene; indene and phenaline.

A wide variety of alcohols may be used in the process according to the present invention; the alcohol may be mono- or polyhydric, may be primary, secondary or tertiary and may be aliphatic, cycloaliphatic or aromatic. Monohydric alcohols having in the range of from 1 to 20 carbon atoms per molecule and, particularly, alkanols, are preferred. Very good results have been obtained with methanol. Other examples of suitable alcohols are ethanol, propanol, butanol, pentanol, hexanol, heptanol, octanol, nonanol, decanol, ethylene glycol, diethylene glycol, propylene glycol, ethylene glycol monoalkyl ethers (the alkyl group having up to, for example, 10 carbon atoms), 1,3-butanediol, cyclohexanol, phenol, benzyl alcohol, 2-naphthol and 2-phenanthrol.

The acid portion of the diester obtained according to the present invention is derived from the optionally substituted ethylenically unsaturated hydrocarbon and the alcohol portion of the diester is derived from the alcohol. Accordingly, ethylene, methanol and carbon monoxide are converted into dimethyl succinate; propene, ethanol and carbon monoxide into diethyl 2-methylbutanedioate; 2-butene, methanol and carbon monoxide into dimethyl 2,3-dimethylbutanedioate, and isobutene, methanol and carbon monoxide into dimethyl 3-methylpentanedioate.

The process according to the invention can be carried out batchwise, semi-continuously or continuously. The reaction time varies in relation to the temperature used and is usually between 0.5 and 20 hours.

The following Examples are intended to illustrate the invention and are not to be construed as limiting the invention.

EXAMPLES 1-9

The Examples 1-9 were carried out in a 300 ml autoclave made of Hastelloy C ("Hastelloy" is a trade name) provided with a magnetically driven stirrer. In all experiments, the autoclave was charged with palladium-(II) acetate (0.1 mmol), methanol (10 ml, 247 mmol) and diglyme (50 ml). The autoclave was further charged with a quinone and a redox agent (except in Example 10), flushed with carbon monoxide, charged with carbon monoxide, ethylene and, in four Examples with air, all this as detailed in the Table hereinafter, heated to the temperature stated in the Table and kept at this temperature for the time also stated in the Table. Then, the amounts of dimethyl succinate and quinone (or oxygen where air has been used) in the reaction mixture were determined. The only by-products which could be detected were methyl acrylate and methyl 3-methoxypropionate, which were formed in a total amount of less than 2% mol, calculated on dimethyl succinate. The table also presents the conversion of the quinone and the yield of dimethyl succinate in mmol.

Comparison of Examples 1 and 2 shows that the presence of oxygen in Example 2 enhances the yield of dimethyl succinate.

Comparison of Examples 1 and 3 shows that the presence of chloranil allows a higher yield of dimethyl succinate than that of p-benzoquinone.

Comparison of Examples 2 and 7 shows the enhancing effect of a redox agent on the yield of dimethyl succinate.

Examples 4 and 6 show that cupric chloride and Examples 5, 8 and 9 show that vanadyl sulfate, ferrous perchlorate and manganese sulphate are suitable redox agents.

COMPARATIVE EXPERIMENT

An experiment was carried out which differed from Example 2 only in that no quinone was present. No reaction was observed after 1 h at 90° C. Subsequently, after 3 h at 100° C. only 5 mmol of dimethyl succinate had been formed.

EXAMPLE 13

An experiment was carried out in the manner of Example 1, starting from palladium(II) acetate (0.1 mmol), methanol (10 ml, 247 mmol), diglyme (50 ml), chloranil (50 mmol), cupric tosylate (2 mmol), isobutene (5 ml, 49

TABLE

| Example | Quinone mmol | Redox agent mmol | Pressure, bar, $C_2H_4$ | CO | air | Reaction time, h | Temperature, °C. | Conversion quinone ($O_2$ in air), % | Yield of dimethyl succinate, mmol |
|---|---|---|---|---|---|---|---|---|---|
| 1 | chloranil 50 | Cu(tosylate)$_2$ 2.0 | 10 | 20 | 0 | 2 | 90 | 75 | 37.5 |
| 2 | chloranil 50 | Cu(tosylate)$_2$ 2.0 | 10 | 20 | 20 | 5 | 80 | (100) | 55 |
| 3 | p-benzoquinone 50 | Cu(tosylate)$_2$ 2.0 | 10 | 20 | 0 | 5 | 90 | 38 | 19 |
| 4 | chloranil 50 | CuCl$_2$ 2.0 | 10 | 20 | 0 | 0.75 | 90 | 60 | 30 |
| 5 | chloranil 50 | VOSO$_4$ 2.0 | 10 | 20 | 0 | 1 | 90 | 73 | 36.5 |
| 6 | chloranil 50 | CuCl$_2$ 2.0 | 20 | 20 | 0 | 1.5 | 90 | 78 | 39 |
| 7 | chloranil 50 | none | 10 | 20 | 20 | 5 | 80 | (100) | 43 |
| 8 | chloranil 50 | Fe(ClO$_4$)$_2$ 2.0 | 10 | 20 | 0 | 1 | 90 | 73 | 36.5 |
| 9 | chloranil 50 | MnCl$_2$ 2.0 | 10 | 20 | 20 | 5 | 80 | (100) | 40 |
| 10 | chloranil 50 | Cu(CF$_3$SO$_3$H)$_2$ 2.0 | 10 | 20 | 20 | 2.5 | 90 | (100) | 70 |

EXAMPLE 11

An experiment was carried out in the manner of Examples 1-9, starting from palladium(II) acetate (0.1 mmol), methanol (10 ml, 247 mmol), diglyme (50 ml), chloranil (50 mmol), cupric tosylate (2 mmol), 1-octene (20 mmol), carbon monoxide (20 bar) and air (20 bar). The autoclave was kept for 5 h at a temperature of 80° C.

The conversions of the molecular oxygen and the 1-octene were 100% and 55%, respectively, with a selectivity to dimethyl C$_6$-butanedioates of 79% (the content of n-hexylbutanedioate being 85%), to methyl hydrogen C$_6$-butanedioates of 16% and to methyl n-nonenoates of 5%. The selectivity to a certain compound, expressed in a percentage, is defined herein as 100×a/b in which "a" is the amount of starting ethylenically unsaturated compound that has been converted into that certain compound "b" is the total amount of starting ethylenically unsaturated compound that has been converted.

EXAMPLE 12

The experiment of Example 11 was repeated except that 20 ml of 1-dodecene instead of 20 ml of 1-octene was used.

The conversions of the molecular oxygen and 1-dodecene were 100% and 64%, respectively, with a selectivity to dimethyl C$_{10}$-butanedioate of 83% (the content of n-decylbutanedioate being 85%), to methyl hydrogen C$_{10}$-butanedioates of 12% and to methyl n-tridecenoates of 5%.

mmol), carbon monoxide (20 bar) and air (20 bar). The autoclave was kept for 5 h at a temperature of 80° C.

Dimethyl 3-methylpentanedioate and methyl 3-methyl-3-butenoate were formed in a yield of 20 and 33%, respectively.

EXAMPLE 14

The experiment of Example 13 was repeated with the difference that cupric chloride (2 mmol) instead of cupric tosylate (2 mmol) were used.

Dimethyl 3-methylpentanedioate and methyl 3-methyl-3-butenoate were formed in a yield of 47 and 6%, respectively.

I claim:

1. A process for the preparation of a diester of a dicarboxylic acid which process comprises reacting at a temperature in the range of from 20° C. to 200° C. and a pressure in the range of from 5 to 200 bar an ethylenically unsaturated hydrocarbon having two carbon atoms per molecule less than said dicarboxylic acid, carbon monoxide and an alcohol in the presence of:
   (a) a noble metal selected from the group consisting of Group VIII of the Periodic Table of the Elements and compounds thereof, and
   (b) a quinone.

2. The process of claim 1 wherein said ethylenically unsaturated hydrocarbon is selected from the group consisting of substituted ethylenically unsaturated hydrocarbons and unsubstituted ethylenically unsaturated hydrocarbons.

3. The process of claim 2 wherein said process is carried out in the presence of palladium and/or a compound of palladium.

4. The process of claim 2 wherein said process is carried out in the presence of palladium compound.

5. The process of claim 3 wherein said palladium compound is a Pd(II) salt of an alkanoic acid having not more than 12 carbon atoms per molecule.

6. The process of claim 5 said palladium compound is palladium(II) acetate.

7. The process of claim 2 wherein the quinone is a benzoquinone selected from the group consisting of substituted benzoquinone and unsubstituted benzoquinone benzoquinone.

8. The process of claim 7 wherein the benzoquinone is a p-benzoquinone.

9. The process of claim 8 wherein the p-benzoquinone is a halogen-substituted p-benzoquinone.

10. The process of claim 9 wherein the p-benzoquinone is tetrachloro-p-benzoquinone.

11. The process of claim 2 wherein said process is carried out in the presence of a redox agent.

12. The process of claim 11 wherein said redox agent comprises a compound selected from the group consisting of copper, iron, vanadium, cobalt, manganese, and mixtures thereof.

13. The process of claim 12 wherein said redox agent is a cupric compound.

14. The process of claim 13 wherein said cupric compound is cupric tosylate.

15. The process of claim 12 wherein said redox agent is ferrous perchlorate.

16. The process of claim 2 wherein a molar ratio noble metal of Group VIII and/or a compound thereof to ethylenically unsaturated hydrocarbon in the range of from $10^{-2}$ to $10^{-6}$ is used.

17. The process of claim 11 wherein a molar ratio redox agent to noble metal of Group VIII and/or a compound thereof in the range of from 1 to 200 is used.

18. The process of claim 2 wherein it is carried out in the presence of molecular oxygen.

19. The process of claim 18 wherein a molar ratio molecular oxygen to carbon monoxide in the range of from 1:3 to 1:6 is applied.

20. The process of claim 2 wherein a molar ratio carbon monoxide to ethylenically unsaturated hydrocarbon in the range of from 0.5:1 to 10:1 is applied.

21. The process of claim 20 wherein said molar ratio is in the range of from 1:1 to 3:1.

22. The process of claim 2 wherein said process is carried out in the presence of a solvent.

23. The process of claim 22 wherein the solvent is an ether.

24. The process of claim 2 wherein the ethylenically unsaturated hydrocarbon is an alkene having in the range of from 2 to 20 carbon atoms per molecule.

25. The process of claim 2 wherein the ethylenically unsaturated hydrocarbon is a cycloalkene having in the range of from 3 to 20 carbon atoms per molecule.

26. The process of claim 24 wherein the ethylenically unsaturated hydrocarbon is an alkene having in the range of from 2 to 10 carbon atoms per molecule.

27. The process of claim 26 wherein ethylene is used as the starting ethylenically unsaturated hydrocarbon.

28. The process of claim 2 wherein the alcohol is monohydric and has in the range of from 1 to 20 carbon atoms per molecule.

29. The process of claim 28 wherein the alcohol is an alkanol.

30. The process of claim 29 wherein the alkanol is methanol.

* * * * *